United States Patent
Taicher

(10) Patent No.: US 6,586,931 B2
(45) Date of Patent: Jul. 1, 2003

(54) NMR LOGGING IN THE EARTH'S MAGNETIC FIELD

(75) Inventor: Gersh Zvi Taicher, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/839,271

(22) Filed: Apr. 20, 2001

(65) Prior Publication Data

US 2002/0153887 A1 Oct. 24, 2002

(51) Int. Cl.$^7$ ................................................. G01V 3/00
(52) U.S. Cl. ...................................................... 324/303
(58) Field of Search ......................................... 324/303

(56) References Cited

U.S. PATENT DOCUMENTS

| | | | |
|---|---|---|---|
| 2,018,080 A | 10/1935 | Martienssen | 175/182 |
| 2,401,280 A | 5/1946 | Walstrom | 175/182 |
| 2,999,204 A | 9/1961 | Jones et al. | 324/0.5 |
| 3,004,212 A | 10/1961 | Coolidge et al. | 324/0.5 |
| 3,042,855 A | 7/1962 | Brown | 324/0.5 |
| 3,188,556 A | 6/1965 | Worthington | 324/0.5 |
| 3,234,454 A * | 2/1966 | Collins | 324/303 |
| 3,538,429 A | 11/1970 | Baker, Jr. | 324/0.5 |
| 4,035,718 A | 7/1977 | Chandler | 324/0.5 |
| 5,055,787 A * | 10/1991 | Kleinberg et al. | 324/303 |
| 5,578,920 A | 11/1996 | Kuster et al. | 324/301 |
| 5,710,511 A * | 1/1998 | Taicher et al. | 324/303 |
| 5,712,566 A * | 1/1998 | Taicher et al. | 324/303 |
| 5,757,186 A | 5/1998 | Taicher et al. | 324/303 |
| 5,834,936 A * | 11/1998 | Taicher et al. | 324/303 |
| 6,107,797 A * | 8/2000 | Sezginer | 324/303 |
| 6,118,272 A * | 9/2000 | Taicher et al. | 324/303 |
| 6,133,735 A | 10/2000 | Hurlimann et al. | 324/303 |
| 6,166,543 A * | 12/2000 | Sezginer et al. | 324/303 |
| 6,247,542 B1 * | 6/2001 | Kruspe et al. | 166/66 |

OTHER PUBLICATIONS

P. T. Callaghan et al.; *"Earth's Field NMR in Antarctica: A Pulsed Gradient Spin Echo NMR Study of Restricted Diffusion in Sea Ice"*, Journal of Magnetic Resonance, 133, 148–154, 1998.

* cited by examiner

*Primary Examiner*—Edward Lefkowitz
*Assistant Examiner*—Dixomara Vargas
(74) *Attorney, Agent, or Firm*—Madan, Mossman & Sriram, P.C.

(57) ABSTRACT

An apparatus and a method for measurement of NMR relaxation parameters of earth formations uses a coil on a logging tool to substantially polarize nuclear spins within a volume of earth. The polarizing pulse then switched off adiabatically. The magnetization of the spins then precesses around earth's magnetic field at a Larmor frequency corresponding to the earth's field. A second coil on the logging tool is pulsed with a carrier signal having this frequency and modulated by a CPMG sequence to obtain spin echo signals. The spin echo signals may be received by the same coil or by a second coil. Alternatively, beam steering of two coils on the tool may be carried out to ensure a resultant field that has a significant component transverse to the earth's field for carrying out the spin echo measurements.

30 Claims, 2 Drawing Sheets

NMR LOGGING IN THE EARTH'S MAGNETIC FIELD

FIELD OF THE INVENTION

This invention relates to apparatus and techniques for making nuclear magnetic resonance (NMR) measurements in boreholes, and to methods for determining magnetic characteristics of formations traversed by a borehole. Specifically, the invention relates to an NMR tool that has a large region of investigation within the formation as a result of measuring NMR spins at frequencies determined by the earth's magnetic field.

BACKGROUND OF THE INVENTION

A variety of techniques have been used in determining the presence and in estimating quantities of hydrocarbons (oil and gas) in earth formations. These methods are designed to determine formation parameters, including among other things, porosity, fluid content, and permeability of the rock formation surrounding the wellbore drilled for recovering hydrocarbons. Typically, the tools designed to provide the desired information are used to log the wellbore. Much of the logging is done after the wellbores have been drilled. More recently, wellbores have been logged while drilling of the wellbores, which is referred to as measurement-while-drilling ("MWD") or logging-while-drilling ("LWD"). Measurements have also been made when tripping a drillstring out of a wellbore: this is called measurement-while-tripping ("MWT").

One recently evolving technique involves utilizing Nuclear Magnetic Resonance (NMR) logging tools and methods for determining, among other things porosity, hydrocarbon saturation and permeability of the rock formations. The NMR logging tools are utilized to excite the nuclei of the fluids in the geological formations in the vicinity of the wellbore so that certain parameters such as spin density, longitudinal relaxation time (generally referred to in the art as "$T_1$"), and transverse relaxation time (generally referred to as "$T_2$") of the geological formations can be estimated. From such measurements, porosity, permeability, and hydrocarbon saturation are determined, which provides valuable information about the make-up of the geological formations and the amount of extractable hydrocarbons.

A typical NMR tool generates a static magnetic field $B_0$ in the vicinity of the wellbore, and an oscillating magnetic field $B_1$ in a direction perpendicular to $B_0$. This oscillating field is usually applied in the form of short duration pulses. The purpose of the $B_0$ field is to polarize the magnetic moments of nuclei parallel to the static field and the purpose of the $B_1$ field is to rotate the magnetic moments by an angle θ controlled by the width $t_p$ and the amplitude $B_1$ of the oscillating pulse. For NMR logging, the most common sequence is the Carr-Purcell-Meiboom-Gill ("CPMG") sequence that can be expressed as $$TW-90-(t-180-t-\text{echo})_n \quad (1)$$

where TW is a wait time, 90 is a 90 degree tipping pulse, and 180 is a 180 degree refocusing pulse.

After being tipped by 90°, the magnetic moment precesses around the static field at a particular frequency known as the Larmor frequency $\omega_0$, given by $\omega_0 = \gamma B_0$, where $B_0$ is the field strength of the static magnetic field and γ is the gyromagnetic ratio. At the same time, the magnetic moments return to the equilibrium direction (i.e., aligned with the static field) according to a decay time known as the "spin-lattice relaxation time" or $T_1$. Inhomogeneities of the $B_0$ field result in dephasing of the magnetic moments and to remedy this, a 180° pulse is included in the sequence to refocus the magnetic moments. This gives a sequence of n echo signals. These echo sequences are then processed to provide information about the relaxation times.

U.S. Pat. No. 4,350,955 to Jackson et al discloses a pair of permanent magnets arranged axially within the borehole so their fields oppose, producing a region near the plane perpendicular to the axis, midway between the sources, where the radial component of the field goes through a maximum. Near the maximum, the field is homogeneous over a toroidal zone centered around the borehole. With the Jackson arrangement, the axial extent of the region of examination is quite limited. As a result of this, the device can only be operated at relatively low logging speeds: otherwise, because of the tool motion during logging, the magnitude of the static field changes significantly within a fixed region of the formation with an accompanying degradation of NMR signals.

There are several devices in which the problem of limited axial extent of the basic Jackson configuration of permanent magnets is addressed. U.S. Pat. No. 4,717,877 to Taicher et al teaches the use of elongated cylindrical permanent magnets in which the poles are on opposite curved faces of the magnet. The static field from such a magnet is like that of a dipole centered on the geometric axis of the elongated magnets and provides a region of examination that is elongated parallel to the borehole axis. The RF coil in the Taicher device is also a dipole antenna with its center coincident with the geometric axis of the magnet, thereby providing orthogonality of the static and magnetic field over a full 360° azimuth around the borehole.

U.S. Pat. No. 6,023,164 to Prammer discloses a variation of the Taicher patent in which the tool is operated eccentrically within the borehole. In the Prammer device, NMR logging probe is provided with a sleeve having a semi-circular RF shield covering one of the poles of the magnet: the shield blocks signals from one side of the probe. The probe is provided with elements that press the uncovered side of the probe to the sidewall of the borehole so that signals from the uncovered side arise primarily from the formation.

A basic problem with currently used NMR logging tools and methods is that they are based on the generation of a strong magnetic field in the earth formation and operate at frequencies of the order of 1 MHz. The region of investigation is typically no more than a few centimeters inside the formation due to the decay of the static field away from the permanent magnet. A stronger magnetic field, besides being harder to generate, is self-defeating as this pushes up the Larmor frequency to a point where eddy current and dielectric dissipation of the NMR signals become significant. For some tools, the thickness of the region of investigation is of the order of a few millimeters at best because of the spatial variability of the magnetic field. As a result of this, logging is susceptible tool movement in direction perpendicular to borehole axis. For other tools the length of region of investigation along the longitudinal axis is short. As a result of this, logging speed is restricted.

The lack of penetration into the formation means that if a wireline is used for the NMR logging, the logging must be done a short time after drilling to avoid the development of a mudcake. Even if the wireline logging is done a short time after drilling or if a Measurement-while-Drilling method is used, there is still the possibility of invasion of the formation by drilling fluids, so that the logging tool does not measure properties of the virgin formation. Additionally, the drilling process itself usually alter rock formation properties in a close vicinity of a borehole by causing some mechanical damage.

An alternative approach is to use the earth's magnetic field for providing the static field for NMR measurements. The Larmor frequency f for protons at the earth's magnetic field is approximately 2.5 kHz. The signal level per unit volume for an NMR survey is approximately proportional to $f^{7/4}$ which means that the signal per unit volume at 2.5 kHz is reduced to about $25 \times 10^{-6}$ of the value for 1 MHz. However, the earth's magnetic field is uniform everywhere an NMR signal can be generated and received, so that the loss of signal intensity is more than made up by receiving a signal from a much larger volume: this makes it feasible to perform NMR logging wherein the precession frequency is determined by the earth's magnetic field.

U.S. Pat. No. 3,004,212 to Coolidge et al discloses a combined NMR and induction logging tool. An electrical current is passed through a polarizing coil in the shape of an elongated rectangle to produce a polarizing field that is perpendicular to the longitudinal axis of the borehole. This aligns the nuclear spins in the formation parallel to the polarizing field which will be inclined to the earth's magnetic field. Upon switching off the electrical current within a period of 1–10 ms., precession of the nuclear spins about the earth's magnetic field occurs. The signals resulting from the precession may be detected either in the polarizing coil or in a second coil orthogonal to the polarizing coil. Coolidge also teaches the use of stepping down the electrical current from a higher level to a lower level to establish different relaxation conditions on the precession as well as changing the duration of the lower current to plot a rate curve for the nuclear polarization.

U.S. Pat. No. 3,188,556 to Worthington teaches the introduction of a paramagnetic material such as molecular oxygen that is soluble in water to distinguish between the relaxation of protons in an oil phase and of protons in a water phase.

U.S. Pat. No. 3,538,429 to Baker discloses NMR logging in the earth's magnetic field wherein the polarizing coils are configured to suppress 60 Hz. noise without adversely affecting the precession signals from the formation.

U.S. Pat. No. 2,999,204 to Jones et al discloses the use of passing a compensating current in the reverse direction of the polarizing current through the polarizing coil after the polarizing current has been turned off: by properly selecting the magnitude and/or time of the compensating current, it is possible to compensate for dephasing of the precession due to inhomogeneities in the earth's magnetic field. Jones discusses the possible causes of the inhomogeneities as being magnetically retentive material in the earth formations and in the drilling fluid within the borehole. Dephasing of the precession due to magnetic field inhomogeneities causes the magnetic induction signal to decay faster as compared to homogeneous magnetic field.

U.S. Pat. No. 3,042,855 to Brown addresses another problem in NMR logging in the earth's field, namely the strong precession signal produced by borehole fluids. Brown teaches the use of a hollow plastic bag or an expandable bag for enclosing the polarizing and detecting coils with the space around the coil filled with a flowable non-magnetic material. U.S. Pat. No. 4,035,718 to Chandler discloses an alternative arrangement in which the polarizing and detecting coils are enclosed within a nonmagnetic housing containing a colloidal suspension of ferromagnetic particles.

A fundamental problem with the above described teachings is the fact that due to local magnetic field inhomogeneity the precession signals dephase relatively rapidly, without any possibility of forming an echo, making the signals harder to interpret. In addition, there is an additional problem of a dead time following the very fast non-adiabatic turning off the polarizing current during which measurements are dominated by noise. The present invention addresses these problems.

SUMMARY OF THE INVENTION

The present invention is an apparatus and method for performing nuclear magnetic resonance measurements using a borehole tool. A polarizing coil on the tool is activated to align nuclear spins in the earth parallel to the magnetic field produced by the coil. The current in the polarizing coil is turned off adiabatically. The nuclear spins that were aligned parallel to the induced field realign in a direction of earth's magnetic field and precess about the earth's magnetic field with a Larmor frequency corresponding to the earth's field. This frequency is within the audio frequency (AF) band at about 2.7 kHz. A second coil is pulsed with a CPMG sequence (or other suitable sequence) to perform spin echo measurements on precessing spins. The second coil may be used as a receiving antenna for the purpose. Additionally, a third coil may be used for detecting the spin echo signals.

The method may be used in inclined or vertical boreholes. The duration of the polarizing pulse is several times the largest value of $T_1$ of the formation, typically 6 seconds. The turning off of the polarizing pulse is done over a time interval of 100 ms. or more. When two antenna coils are used, the AF signal may be beam-steered to have a direction that is transverse to the earth's magnetic field.

DESCRIPTION OF THE PREFERRED EMBODIMENT

Figure 1:
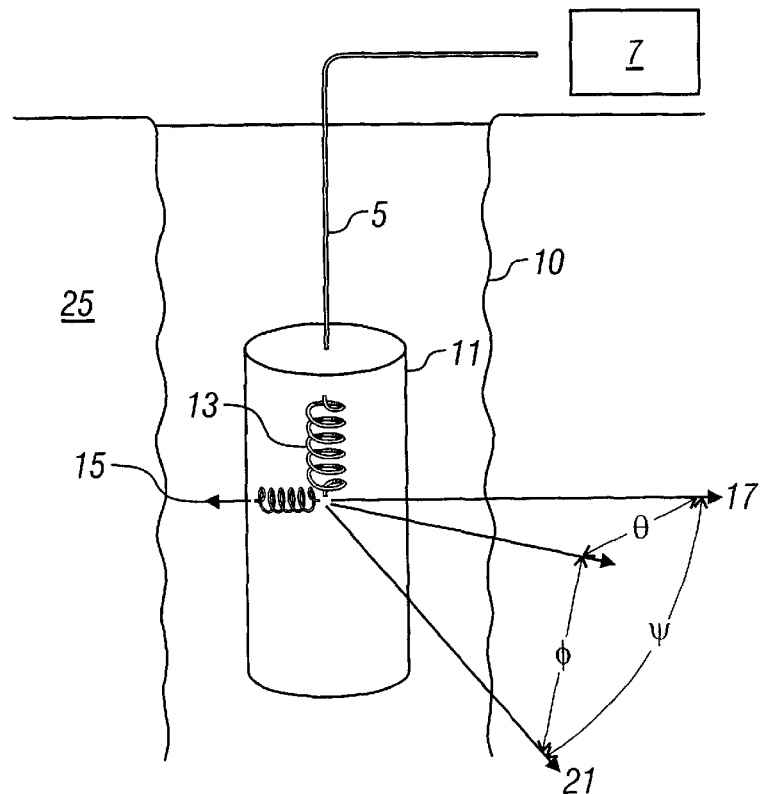
FIG. 1 is a schematic illustration of an NMR tool of the present invention deployed in a borehole.

Referring to FIG. 1, there is shown an NMR tool 11 conveyed in a borehole 10 within earth formations 25. For exemplary purposes, the tool is shown conveyed by a wireline 5. Surface equipment shown at 7 can be of a conventional type and includes a processor that communicates with the downhole equipment. The deployment on a wireline is for illustrative purposes only and the present invention may also be used in Measurement-while-Drilling (MWD) and Logging while tripping (LWT) environments using known prior art configurations.

The tool 11 has a pair of coils 13 and 15 wound on a non-conductive core (not shown). In a preferred embodiment of the invention, the axis of coil 13, referred to as the polarizing coil, is parallel to the longitudinal axis of the tool 11 and the axis 17 of the coil 15, referred to as the excitation coil, is preferably orthogonal to the longitudinal axis of the tool 11 and to the axis of polarizing coil 13. As will be apparent from the description of the operation of the tool below, this orthogonality and requirement that the axis of coil 13 is parallel to the longitudinal axis of the tool 11 is not essential.

As shown in FIG. 1, the tool 11 is in a vertical portion of the borehole and the axis 17 of the excitation coil lies in a horizontal plane. This is a matter of convenience only and in general, in an inclined borehole, the tool is characterized by a toolface orientation and the borehole dip and azimuth. For convenience, the axis 17 may be used to define the toolface orientation. Also shown in FIG. 1 is the direction 21 of the earth's magnetic field. This direction 21 of the earth's magnetic field is at an azimuth θ relative to the axis 17 and a relative dip angle φ relative to the axis 17. When the borehole is vertical, it is clear that the angle φ will also be the absolute dip (or inclination) of the earth's magnetic field.

A few comments are in order about the angle φ. The magnetic inclination (or dip) is that angle that the geomagnetic field is tilted with respect to the surface of the earth. Magnetic inclination varies from 90° (perpendicular to the surface of the earth) at the magnetic poles to 0° (parallel to the surface) at the magnetic equator. In the Northern Hemisphere, the acute angle that the magnetic field forms at the surface of the earth points towards the North Magnetic Pole. The opposite is true in the Southern Hemisphere. The inclination generally increases with the latitude. For example, it is approximately 72° 24' at Toronto, Ontario and is approximately 64° at Atlanta, Ga. Thus, except at locations close to the magnetic equator, the earth's magnetic field has a significant vertical component.

Referring again to FIG. 1, the angle ψ between the axis 17 and the earth's magnetic field 21 is given by the relation $$\text{Cos } \psi = \text{Cos } \theta \text{Cos } \phi \quad (2)$$

When an electrical current is passed through the polarizing coil 13, this produces a magnetic field in the earth formation 25 in the vicinity of the tool that is parallel to the coil axis. The resultant magnetic field in the earth formation is given by the vector sum of the earth's field and the field produced by the polarizing coil. The polarizing coil 13 and the current therein are selected so that the induced field due to the polarizing coil is much greater than the earth's magnetic field. The field strength of the earth's magnetic field is approximately 65 μT while the induced field is of the order of several mT. The induced field has a typical $1/r^2$ to $1/r^3$ decrease in field strength with distance from the coil, so that in a large volume of the earth formation in the vicinity of the borehole, the resultant magnetic field is closely aligned with the field induced by the polarizing coil.

The current in the polarizing coil is kept on for a time equal to a few times the largest $T_1$ value of the earth formation. Typically, the duration of the polarizing pulse is 6 seconds. As a result of this polarizing pulse, nuclear spins in the earth formation 25 that are originally aligned parallel to the earth's magnetic field 21 will become re-oriented substantially parallel to the polarizing field, i.e., substantially parallel to the coil axis. The polarizing current is then turned off adiabatically. As a result of this, the magnetic field direction becomes that of the earth's magnetic field. The condition for adiabatic change of the field direction is, in general, that the direction has to change slowly compared with the instantaneous Larmor frequency. The Larmor frequency at the earth's field is about 2.7 kHz while with a field strength of 10 mT for the induced field, the Larmor frequency is approximately 40 kHz. Therefore, the adiabatic condition is satisfied if the polarizing field is switched off in a time period of about several milliseconds.

As a result of the switching off of the polarizing current, the magnetic field direction is now parallel to the earth's field while having large magnetization due to large induced polarizing field. Consequently, the nuclear spins start precessing about the earth's field at the corresponding Larmor frequency of approximately 2.7 kHz. In the present invention, spin echoes signals are obtained by pulsing the coil 15 with electrical currents at this Larmor frequency which is within the audio frequency (AF) range. A conventional CPMG pulse sequence as given by eq. (1) may be used for the purpose with the same coil being used as a transmitter and a receiver.

Figure 2:
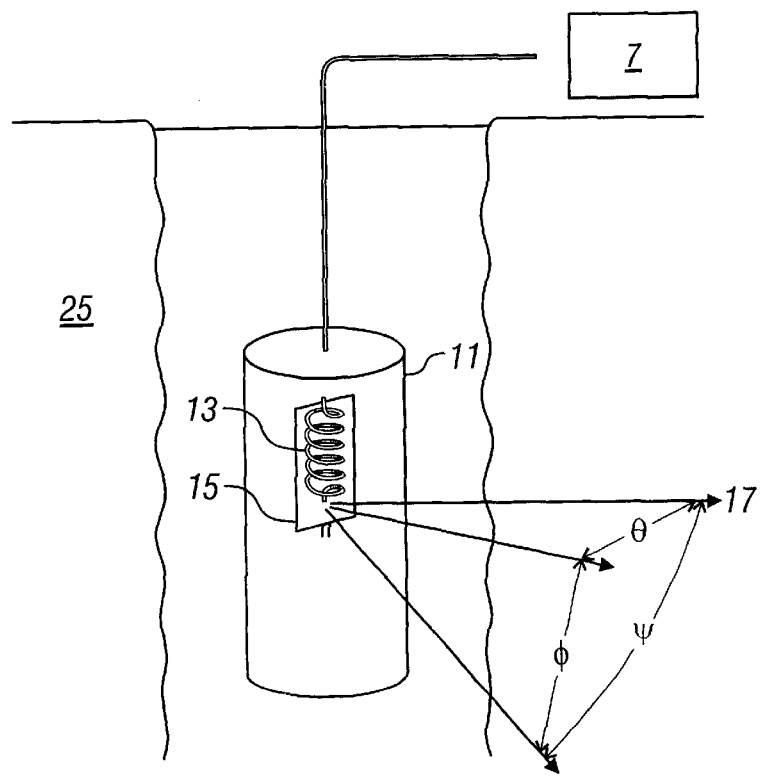
FIG. 2 is a schematic illustration of an alternate embodiment of the NMR tool.

In an alternate embodiment of the invention shown in FIG. 2, transmitter coil 15 is preferably elongated along the longitudinal axis of the borehole and is several times longer than diameter of the borehole 10. In this case this coil generate a substantially two-dimensional magnetic field within the formation of interest. Such a field is perpendicular to the longitudinal axis at any point within the formation of interest and is substantially that of a transverse dipole antenna. This means that RF magnetic field is always orthogonal to the component of the earth's magnetic field along the borehole axis.

Eq. (2) shows that as long as the angle φ is not zero, the angle ψ cannot be zero. This means that except for locations close to the magnetic equator of the earth, the field produced by the transmitter 15 will always have a component orthogonal to the direction of the earth's magnetic field for producing the spin-echo sequence. The analysis of the spin-echo sequence to obtain the $T_2$ distribution of the earth formation may then be carried out using prior art methods. The orthogonality of the two coil axes substantially reduces the current induced in the transmitter/receiver coil by the termination of the polarizing pulse.

It should be noted that FIG. 1 shows the polarizing coil 13 having an axis parallel to the longitudinal axis of the tool and the pulsing coil 15 as having an axis orthogonal to the longitudinal axis of the tool. Those versed in the art would recognize that the coil directions may be interchanged without significant degradation of the performance of the tool as long as the pulsing coil have axial directions that have a component transverse to the earth's magnetic field.

Additionally, the tool may be provided with magnetometers for measuring the earth's magnetic field direction and the logging tool may be provided with a motor (not shown) for rotating the coils relative to tool-face. Using such a motor, it is possible to make the angle θ equal to about 90°. With such an arrangement, the AF magnetic field may be made substantially perpendicular to the earth's magnetic field at any geographical location and for any borehole inclination. As an alternative to the use of a motor, any device (electrical, mechanical, electromechanical or hydraulic) may be used.

Figure 3:
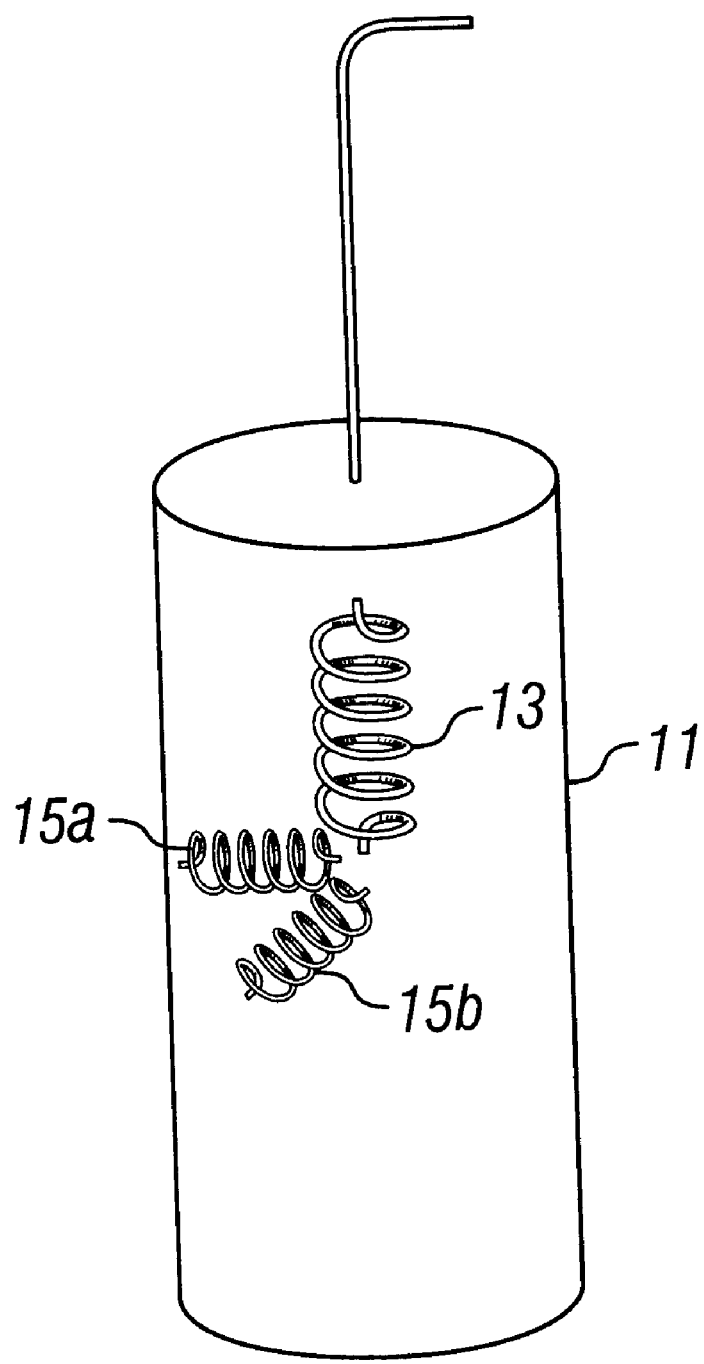
FIG. 3 is a schematic illustration of an alternate NMR tool having two antenna coils for the spin-echo signals.

In an alternate embodiment of the invention shown in FIG. 3, instead of a single transmitter coil 15, a pair of orthogonal coils 15a, 15b are used with the coil axes orthogonal to the tool axis. With such an arrangement and by suitable phase shifting of the currents in the two antennas, the direction of the AF field can be rotated about the longitudinal axis of the tool. With such a configuration, the device and the method of the device may even be used when φ is close to zero. During logging, this type of beam steering may be carried out until the spin-echo signals are observed to have a maximum amplitude. Alternatively, the device of FIG. 3 may be used so that coils 15a and 15b are used both as a transmitter and a receiver. One possibility is to use the first coil only as a receiver. The second possibility is to use the second coil also as receiver to detect an additional component of the spin-echo signals, which is orthogonal to the signal component received in the first receiving coil.

Those versed in the art would recognize that with only a single excitation coil as in FIG. 1, the coil axis 17 may be parallel to the magnetic dip direction in deviated boreholes. In such situations, the embodiment of the invention shown in FIG. 3 makes it possible to obtain NMR measurements using the earth's magnetic field.

The long polarization time required in the present invention is not a detriment since the tool is a low resolution tool with a large volume of investigation. At a logging speed of 30 ft/min, six seconds of polarization time would correspond to a motion of the tool of 3 ft. This is small in comparison to the axial (and radial) extent of the region of investigation.

The method of the present invention has been discussed above using an example of a CPMG sequence. U.S. Pat. No. 6,163,153 to Itskovich et al, the contents of which are fully incorporated here by reference, teaches the use of a modified pulse sequence in which the refocusing pulse has a tipping angle that is less than 180°, and may be between 90° and 180°. The method of the present invention may also be used with such modified pulse sequences.

The method and the apparatus of the invention have been described for a particular embodiment suitable for use in determining properties of earth formations. However, an equivalent apparatus comprising a polarizing coil and at least one coil for producing pulsed AF signals, may be used for obtaining pulse echo signals from other objects, such as a human body.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method for determining a parameter of interest of a volume of earth formation with a borehole tool conveyed in a borehole within the formation, the method comprising;
    (a) pulsing a first coil on the borehole tool with a polarizing signal and aligning nuclear spins within said volume substantially parallel to a direction of a magnetic field produced thereby in said volume;
    (b) adiabatically discontinuing the polarizing signal and allowing said nuclear spins to reorient towards a direction parallel to a magnetic field of the earth;
    (c) pulsing a second coil on the borehole tool with a sequence of pulses for exciting nuclei within said volume; and
    (d) detecting nuclear magnetic resonance spin echo signals from said excited nuclei;
    (e) providing in response to said signals an output indicative of said parameter of interest of the volume of earth formation.

2. The method of claim 1 wherein said borehole has an axis inclined to a vertical direction.

3. The method of claim 1 wherein said polarizing signal has a duration several time greater than a spin-lattice relaxation time $T_1$ of said volume of earth formation.

4. The method of claim 1 wherein said polarizing signal has a duration greater than 6 seconds.

5. The method of claim 1 wherein adiabatically discontinuing the polarizing signal further comprises switching off the polarizing signal over a time interval greater than 5 ms.

6. The method of claim 1 wherein pulsing said second coil further comprises:
    (i) passing a carrier current having a frequency through said second coil, and
    (ii) modulating said carrier current using a pulse sequence selected from: (A) a CPMG pulse sequence, and, (B) a modified CPMG pulse sequence having a refocusing pulse with a tipping angle between 90° and 180°.

7. The method of claim 6 wherein said frequency is substantially equal to a Larmor frequency of hydrogen nuclei in earth's magnetic field.

8. The method of claim 1 wherein detecting said spin echo signals further comprises using the second coil.

9. The method of claim 1 wherein detecting said spin echo signals further comprises using a third coil on the borehole tool having an axis orthogonal to the axes of the first and second coils.

10. The method of claim 6 further comprising:
    (i) providing a third coil on the borehole tool, said third coil having an axis substantially orthogonal to the axes of the first and second coils,
    (ii) passing a current through the third coil having a phase relative to a phase of the current through the second coil,
    (iii) modulating said current through the third coil with said CPMG sequence, and
    (iv) adjusting said phase of the current in the third coil to increase an amplitude of said spin echo signals.

11. The method of claim 1 wherein said parameter of interest further comprises a spin—spin ($T_2$) distribution of said earth formation.

12. The method of claim 1 wherein said borehole tool is conveyed on one of (i) a wireline, (ii) a drillstring, and, (iii) coiled tubing.

13. The method of claim 1 wherein said second coil produces a magnetic field having a direction substantially orthogonal to a direction of a magnetic field produced by the first coil.

14. The method of claim 1 wherein said second coil further comprises a transverse dipole antenna.

15. The method of claim 1 further comprising:
    (i) rotating the tool and making a magnetic field of the second coil orthogonal to a direction of the earth's magnetic field.

16. A method for determining a parameter of interest of a material in a region of investigation, the method comprising;
    (a) pulsing a first coil with a polarizing signal and aligning nuclear spins within said region of investigation substantially parallel to a direction of a magnetic field produced thereby in said region;
    (b) adiabatically discontinuing the polarizing signal and allowing said nuclear spins to reorient towards a direction parallel to a magnetic field of the earth;
    (c) pulsing a second coil with a sequence of pulses for exciting nuclei within said region; and
    (d) detecting nuclear magnetic resonance signals from said excited nuclei;
    (e) providing in response to the detected nuclear magnetic resonance signal an output indicative of said parameter of interest of a material in said region of investigation.

17. A borehole tool for determining a parameter of interest of a volume of earth formation surrounding the borehole, the tool comprising:
    (a) a first antenna for producing a static magnetic field in said volume for a duration selected for substantially polarizing nuclear spins within said volume and causing said polarized nuclear spins to precess about a direction of earth's magnetic field thereafter;
    (b) a second antenna for producing a pulsed magnetic field having a direction with a component transverse to said direction of earth's magnetic field, said second antenna pulsed with an AF signal modulated by a pulse sequence for forming spin echo signals in said volume.

18. The borehole tool of claim 17 wherein the second antenna has an axis substantially orthogonal to an axis of the first antenna.

19. The borehole tool of claim 18 further comprising a third antenna having an axis substantially orthogonal to the axes of the first antenna and the second antenna.

20. The borehole tool of claim 17 wherein said duration is several time greater than a spin-lattice relaxation time $T_1$ of said volume of earth formation.

21. The borehole tool of claim 17 wherein said duration is greater than 6 seconds.

22. The borehole tool of claim 17 wherein, after said duration, said first antenna is switched off over a time interval greater than 5 ms.

23. The borehole tool of claim 17 wherein pulsing said second antenna is pulsed with a pulse sequence selected from: (i) a CPMG pulse sequence, and, (ii) a modified CPMG pulse sequence having a refocusing pulse with a tipping angle between 90° and 180°.

24. The borehole tool of claim 17 wherein said AF signal has a carrier frequency substantially equal to a Larmor frequency of hydrogen nuclei in earth's magnetic field.

25. The borehole tool of claim 17 wherein said second antenna is further adapted for detecting said spin echo signals.

26. The borehole tool of claim 17 further comprising a third antenna for detecting said spin echo signals.

27. The borehole tool of claim 17 further comprising a third antenna pulsed with modulated AF signal having a phase that is adjustable relative to a phase of the modulated AF signal in the second antenna.

28. The borehole tool of claim 17 wherein said borehole tool is conveyed on one of (i) a wireline, (ii) a drillstring, and, (iii) coiled tubing.

29. The borehole tool of claim 17 further comprising:
(i) a device for rotating the tool and making a magnetic field of the second antenna have a component orthogonal to a direction of the earth's magnetic field.

30. An apparatus for determining a parameter of interest of a material in a region of investigation, the apparatus comprising:

(a) a first antenna for producing a static magnetic field in said region of investigation for a duration selected for substantially polarizing nuclear spins within said region and causing said polarized nuclear spins to precess about said direction of earth's magnetic field thereafter;

(b) a second antenna for producing a pulsed magnetic field having a direction with a component transverse to said direction of earth's magnetic field, said second antenna pulsed with an AF signal modulated by a pulse sequence for forming spin echo signals in said volume.

* * * * *